US012708181B2

(12) United States Patent
Schwartz et al.

(10) Patent No.: US 12,708,181 B2
(45) Date of Patent: Aug. 18, 2026

(54) SYSTEMS AND METHODS FOR PROVIDING A USER PORTAL TO FACILITATE MODELING OF FOOT-RELATED DATA

(71) Applicant: Aetrex, Inc., Teaneck, NJ (US)

(72) Inventors: Laurence I. Schwartz, New York, NY (US); Kumar Rajan, Clinton, NJ (US); Alexander Choy, Fort Lee, NJ (US); Wendy Fan, Teaneck, NJ (US)

(73) Assignee: Aetrex, Inc., Teaneck, NJ (US)

( * ) Notice: Subject to any disclaimer, the term of this patent is extended or adjusted under 35 U.S.C. 154(b) by 399 days.

(21) Appl. No.: 18/209,238

(22) Filed: Jun. 13, 2023

(65) Prior Publication Data

US 2023/0397695 A1 Dec. 14, 2023

Related U.S. Application Data

(60) Provisional application No. 63/351,701, filed on Jun. 13, 2022.

(51) Int. Cl.

*A43D 1/02* (2006.01)
*A61B 5/00* (2006.01)
*A61B 5/107* (2006.01)

(52) U.S. Cl.

CPC ............ *A43D 1/025* (2013.01); *A61B 5/1074* (2013.01); *A61B 5/7445* (2013.01); *A43D 1/027* (2013.01)

(58) Field of Classification Search

CPC ...... A43D 1/025; A43D 1/027; A61B 5/1074; A61B 5/7445

USPC ........................................................... 33/512

See application file for complete search history.

(56) References Cited

U.S. PATENT DOCUMENTS 8,152,744 B2 * 4/2012 Mukumoto .............. A43B 7/28 600/592
D732,055 S * 6/2015 Schwartz ..................... D14/486
9,760,674 B2 * 9/2017 Schouwenburg ..... B29C 64/393
10,327,502 B2 * 6/2019 Schouwenburg .... A43B 17/006
10,463,257 B2 * 11/2019 Schwartz ............. H04N 13/243
10,528,032 B2 * 1/2020 Schouwenburg ..... B29C 64/386
11,154,243 B2 * 10/2021 Esposito .................. A61B 5/01
11,260,597 B2 * 3/2022 Schouwenburg ...... B33Y 50/00
2007/0011173 A1 * 1/2007 Agostino ................ G06F 16/00
2014/0285646 A1 * 9/2014 Kahlon .................. A43D 1/025 348/77
2016/0101571 A1 * 4/2016 Schouwenburg ...... B33Y 50/00 602/5
2020/0151594 A1 * 5/2020 Schwartz ............. A61B 5/7267
2021/0279900 A1 * 9/2021 Schwartz ................ G06T 7/593
2022/0036572 A1 * 2/2022 Schwartz ............. A61B 5/6829
2023/0022065 A1 * 1/2023 Schwartz ............... A43D 1/025
2023/0397695 A1 * 12/2023 Schwartz ............. A61B 5/1074
2025/0248620 A1 * 8/2025 Schwartz ............. A61B 5/6829

FOREIGN PATENT DOCUMENTS

WO WO-2023205083 A1 * 10/2023 ............. G06T 19/20

* cited by examiner

*Primary Examiner* — Peter J Macchiarolo
*Assistant Examiner* — Anna Josephine Saunders
(74) *Attorney, Agent, or Firm* — Lowenstein Sandler LLP

(57) ABSTRACT

Methods, systems, and non-transitory computer readable media for providing a user portal to facilitate modeling of foot-related data are described.

20 Claims, 8 Drawing Sheets

SYSTEMS AND METHODS FOR PROVIDING A USER PORTAL TO FACILITATE MODELING OF FOOT-RELATED DATA

CROSS-REFERENCE TO RELATED APPLICATION(S)

This application claims the benefit of priority of U.S. Provisional Patent Application No. 63/351,701, filed on Jun. 13, 2022, the disclosure of which is hereby incorporated by reference herein in its entirety.

TECHNICAL FIELD

The present disclosure relates to systems and methods for modeling anatomy.

BACKGROUND

A foot last is a mechanical form shaped like a human foot that is used in the assembly, manufacture, and repair of shoes. The design of foot lasts is generally based on target shoe sizes, but generally does not take into account various other foot-related measurements or geographical variations of foot shape.

BRIEF DESCRIPTION OF THE DRAWINGS

The present disclosure is illustrated by way of example, and not by way of limitation in the figures of the accompanying drawings.

DETAILED DESCRIPTION

Figure 1:
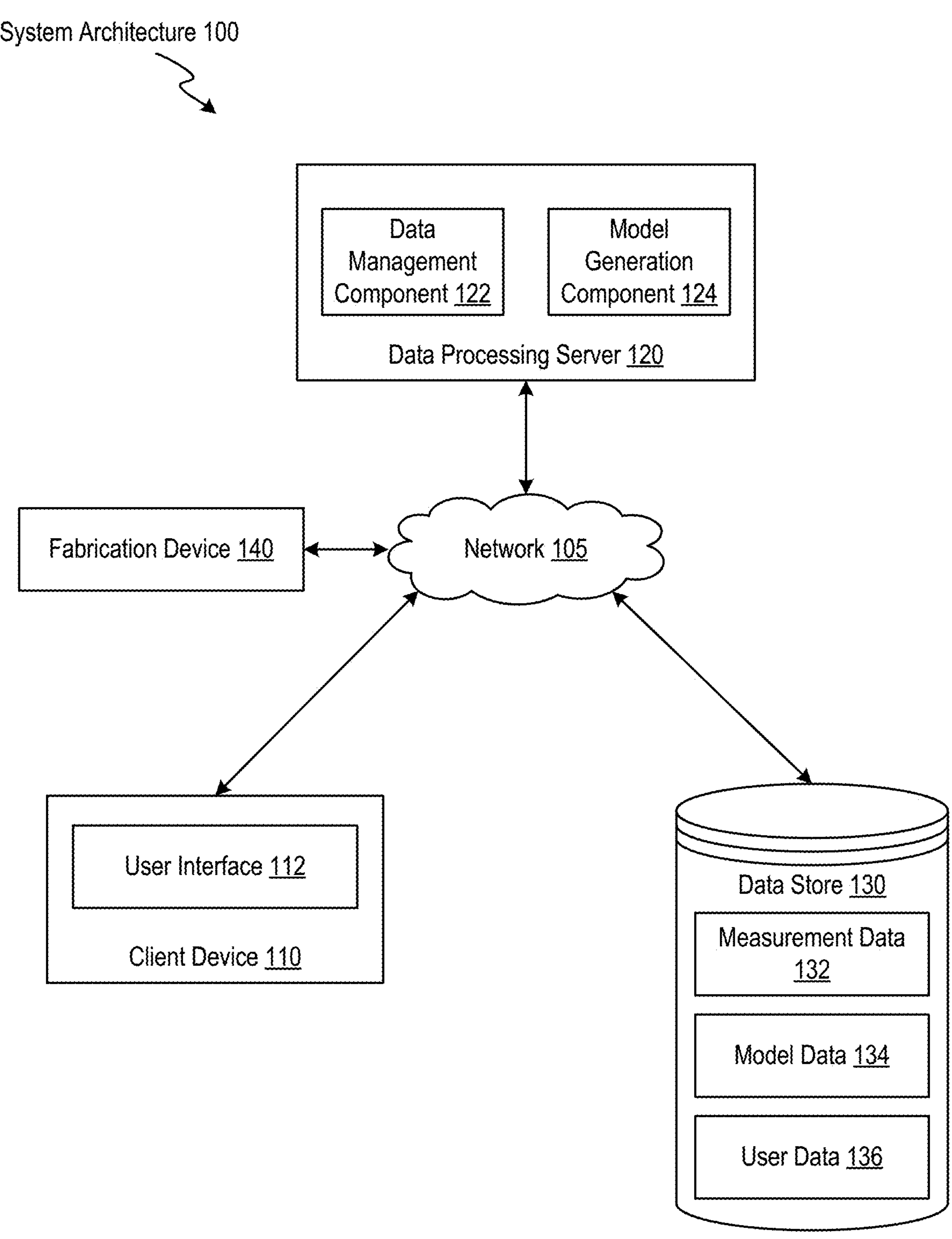
FIG. 1 is a block diagram illustrating an exemplary system architecture in accordance with at least one embodiment.

Described herein are technologies that facilitate data-driven approaches to generating human foot models and models of foot lasts to, for example, facilitate shoe fabrication and/or shoe recommendations. Specifically, certain embodiments described herein relate to a graphical user interface (GUI) that presents a user with selectable data elements representative of statistical foot measurement data. The user can select desired measurements, which can be filtered, for example, by selecting various parameters such as a gender indicator or a geographical indicator. The user may further select subsets of data within each statistical data set. Once selected, the system can identify a pre-existing 3D model of a foot or generate a new 3D model of the foot that best fits the selected data. In addition, or alternatively, the system may identify or generate a 3D model of a foot last that best fits the selected data. The resulting 3D model may be generated for display in the portal for inspection, and/or transmitted to a fabrication device (such as a 3D printer). The embodiments described herein advantageously provide a fast, easy-to-use portal to allow shoe manufacturers to identify and utilize relevant data in the design of foot lasts, as well as identifying relevant products in their own inventories.

Based on geographic region, gender, shoe size, and percentile scores of one or more relevant foot measurements (e.g., length, width, girth, arch height, dorsal height, ankle girth, ball girth, ball height, ball width, heel width, instep width, length to first metatarsal head, length to fifth metatarsal head, long heel girth, short heal girth, and max toe height), the embodiments described herein utilize, for example, a nearest neighbor algorithm to identify a model of a foot or foot last that is a close or best fit to matching the selected criteria. Certain embodiments advantageously utilize machine learning models to identify several key anatomical points on the foot, including but not limited to, the pternion, the junction point, the ball point, the metatarsal tibialis, the metatarsal fibularis, and the acropodion, which can be used to facilitate identification of close or best fit models, as well as identify key locations of the models for modification/deformation via rigid object transformation algorithms to improve the fit. Moreover, based on the positions of these anatomical points, the models can be characterized into user-defined categories, and can be used to generate foot lasts.

In addition to the measurements computed for every foot model, the embodiments herein further provide the ability to identify any cross-section of the foot or foot last model using five degrees of freedom: three coordinate axes, pitch, and roll, from which additional measurements (including outer perimeter) can be computed.

Further, the embodiments described herein may be implemented as an application program interface that could be used to further identify best fit products for a target demographic within a company's own inventory. For example, the embodiments described herein may be used to identify a close or best fit foot last 3D model based on a set of target parameters, which can be used to identify products having been manufactured based on that foot last.

System Architecture

Exemplary implementations of the embodiments of the present disclosure are now described. FIG. 1 illustrates an exemplary system architecture 100 in accordance with at least one embodiment. The system architecture 100 includes a client device 110, a data processing server 120, a data store 130, and a fabrication device 140, with each device of the system architecture 100 being communicatively coupled via a network 105. One or more of the devices of the system architecture 100 may be implemented using a generalized computer system 400, described with respect to FIG. 4. The devices of the system architecture 100 are merely illustrative, and it is to be understood that other user devices, data processing servers, data stores, and networks may be present.

In one embodiment, network 105 may include a public network (e.g., the Internet), a private network (e.g., a local area network (LAN) or wide area network (WAN)), a wired network (e.g., Ethernet network), a wireless network (e.g., an 802.11 network or a Wi-Fi network), a cellular network (e.g., a Long Term Evolution (LTE) network), routers, hubs, switches, server computers, and/or a combination thereof. Although the network 105 is depicted as a single network, the network 105 may include one or more networks operating as stand-alone networks or in cooperation with each other. The network 105 may utilize one or more protocols of one or more devices to which they are communicatively coupled.

In one embodiment, the client device 110 (which may also be referred to as a "user device") may include a computing device such as a personal computer (PC), laptop, mobile phone, smart phone, tablet computer, netbook computer, etc. An individual user may be associated with (e.g., own and/or operate) the client device 110. As used herein, a "user" may be represented as a single individual. However, other embodiments of the present disclosure encompass a "user" being an entity controlled by a set of users and/or an automated source. For example, a set of individual users federated as a community in a company or government organization may be considered a "user." In at least one embodiment, the user is the individual who seeks to receive information descriptive of physical parameters of their feet.

The client device 110 may utilize one or more local data stores, which may be internal or external devices, and may each include one or more of a short-term memory (e.g., random access memory), a cache, a drive (e.g., a hard drive), a flash drive, a database system, or another type of component or device capable of storing data. The local data stores may also include multiple storage components (e.g., multiple drives or multiple databases) that may also span multiple computing devices (e.g., multiple server computers). In at least one embodiment, the local data stores may be used for data back-up or archival purposes.

The client device 110 may implement a user interface 112, which may allow the client device 110 to send/receive information to/from other client devices (not shown), the data processing server 120, the data store 130, and the fabrication device 140. The user interface 112 may be a graphical user interface (GUI). For example, the user interface 112 may be a web browser interface that can access, retrieve, present, and/or navigate content (e.g., web pages such as Hyper Text Markup Language (HTML) pages) provided by the data processing server 120. In one embodiment, the user interface 112 may be a standalone application (e.g., a mobile "app," etc.), that enables a user to use the client device 110 to send/receive information to/from other client devices (not shown), the data processing server 120, the data store 130, and the fabrication device 140. An exemplary user interface is illustrated in FIGS. 2A-2E, which provides a portal to facilitate modeling of foot-related data.

In one embodiment, the data processing server 120 may include one or more computing devices (such as a rack-mount server, a router computer, a server computer, a personal computer, a mainframe computer, a laptop computer, a tablet computer, a desktop computer, etc.), data stores (e.g., hard disks, memories, databases), networks, software components, and/or hardware components from which digital contents may be retrieved. In at least one embodiment, the data processing server 120 may be a server utilized by the client device 110, for example, to provide the client device 110 with measurement and modeling data. In at least one embodiment, additional data processing servers may be present. In at least one embodiment, the data processing server 120 utilizes a data management component 122 to process, store, and analyze statistical measurement data 132 (which may be stored in the data store 130). In at least one embodiment, the data processing server further utilizes a model generation component 124 to identify, generate, and/or modify 3D models of the foot and/or foot lasts based on measurement data selected by a user of the user interface 112, which may be stored as model data 134 in the data store 130. In at least one embodiment, various models stored in the model data 134 may have been previously generated from scans of individuals' feet, and may have associated metadata describing various parameters associated therewith, including foot measurements, gender, and geographic location. In at least one embodiment, the metadata may be used for identification of models based on selected sets of statistical data, as described further below. Systems and methods for generating, modifying, measuring, and characterizing 3D models of feet are disclosed in U.S. Pat. Nos. 10,327,502 B2, 10,463,257 B2, and 11,260,597 B2, as well as U.S. Patent Application Publication Nos. 2020/0151594 A1, 2023/0022065 A1, and 2022/0036572 A1, the disclosures of which are hereby incorporated by reference herein in their entireties.

In at least one embodiment, the model generation component 124 may utilize one or more machine learning or deep learning models (e.g., a decision tree model or a support vector machine model) to identify or generate the 3D models from the statistical measurement data. The deep learning model may be a deep network that is composed of multiple levels of linear and/or non-linear operations. In at least one embodiment, one or more heuristic models or rule-based models may be used in addition to or in lieu of the deep learning models. In at least one embodiment, the model generation component 124 includes a machine learning engine that uses compiled and stored data in the data store 130 (e.g., the measurement data 132 and or the model data 134 and associated metadata) to train a machine learning model. The machine learning engine may partition historical 3D model data into a training set (e.g., ninety percent of the historical feet data). The partitioning of the historical 3D model data may be via k-fold cross-validation.

In k-fold cross-validation, an original sample (e.g., 3D model data 134) may be randomly partitioned into k equal sized subsamples. Of the k subsamples, a single subsample is retained as the validation data for testing the model, and the remaining k−1 subsamples are used as training data. The cross-validation process is then repeated k times, with each of the k subsamples used exactly once as the validation data. The k results can then be averaged to produce a single estimation. Observations may be used for both training and validation, and each observation may be used for validation exactly once. In at least one embodiment, 10-fold cross-validation may be used. In at least one embodiment, k may be an unfixed parameter. For example, setting k=2 results in 2-fold cross-validation. In 2-fold cross-validation, the dataset is randomly shuffled into two sets d0 and d1, so that both sets are equal size (which may be implemented by shuffling the data array and then splitting it in two). Training may be on d0 and validating may be on d1, followed by training on d1 and validating on d0. In at least one embodiment, the folds are selected so that the mean response value is approximately equal in all the folds. In the case of binary classification, each fold may contain roughly the same proportions of the two types of class labels. In at least one embodiment, scores are generated based on target values, with the target values corresponding to metrics such as one or more of area, pressure distribution, max weight, arch depth, dorsal height, length, width, arch type, etc. Training data may include best-fit scores, which may be learned based on defined rules used to predict best fits of statistical data.

In at least one embodiment, the machine learning model may use one or more of a decision tree or a support vector machine (SVM). The machine learning model may be composed of a single level of linear or non-linear operations (e.g., SVM) or may be a deep network (e.g., a machine learning model that is composed of multiple levels of non-linear operations). In at least one embodiment, the machine learning model may use an SVM gradient algorithm. The SVM gradient algorithm may be used to predict scores based on gradient boosting regression.

In one embodiment, the data store 130 may include one or more of a short-term memory (e.g., random access memory), a cache, a drive (e.g., a hard drive), a flash drive, a database system, or another type of component or device capable of storing data. The data store 130 may also include multiple storage components (e.g., multiple drives or multiple databases) that may also span multiple computing devices (e.g., multiple server computers). In at least one embodiment, the data store 130 may be cloud-based. One or more of the devices of system architecture 100 may utilize their own storage and/or the data store 130 to store public and private data, and the data store 130 may be configured to provide secure storage for private data. In at least one embodiment, the data store 130 stores user data 136 related to users of the portal, including usernames, login credentials, and other related information pertaining to user sessions. In at least one embodiment, the data store 130 may be used for data back-up or archival purposes.

In one embodiment, the fabrication device 140 may be capable of one or more of injection molding, milling, fused deposition modeling, stereolithography, selective laser sintering, various other types of 3D printing technology, and various other fabrication methods as would be understood by one of ordinary skill in the art. In at least one embodiment, the fabrication device 140 is communicatively coupled to the data processing server 120, and may receive data descriptive a 3D model that is in a format suitable for use by the fabrication device 140, such as an STL file. In at least one embodiment, the fabrication device 140 utilizes a resin, metal material, paper material, or other material for fabricating a foot last model.

Although each of the client device 110, the data processing server 120, the data store 130, and the fabrication device 140 are depicted in FIG. 1 as single, disparate components, these components may be implemented together in a single device or networked in various combinations of multiple different devices that operate together. In at least one embodiment, at least some of the functionality of the data processing server 120 and/or the data store 130 may be performed by the client device 110, or by other devices.

Although embodiments of the disclosure are discussed in the context of foot-related data and modeling, such embodiments are generally applicable to other anatomy and may be useful in the design of other objects that are designed in view of the physical dimensions of such anatomy, such as clothing, protective gear, and medical devices.

Exemplary User Portal Embodiments

FIGS. 2A-2E illustrate an exemplary GUI 200 in accordance with at least one embodiment, which may be implemented by the client device 110 based on data received from the data processing server 120. The GUI 200 includes, for example, an options panel 210 and a data display 220A. In at least one embodiment, a user selection of one of the options from the options panel 210 results in a different set of information presented in the data display 220A.

Figure 2A:
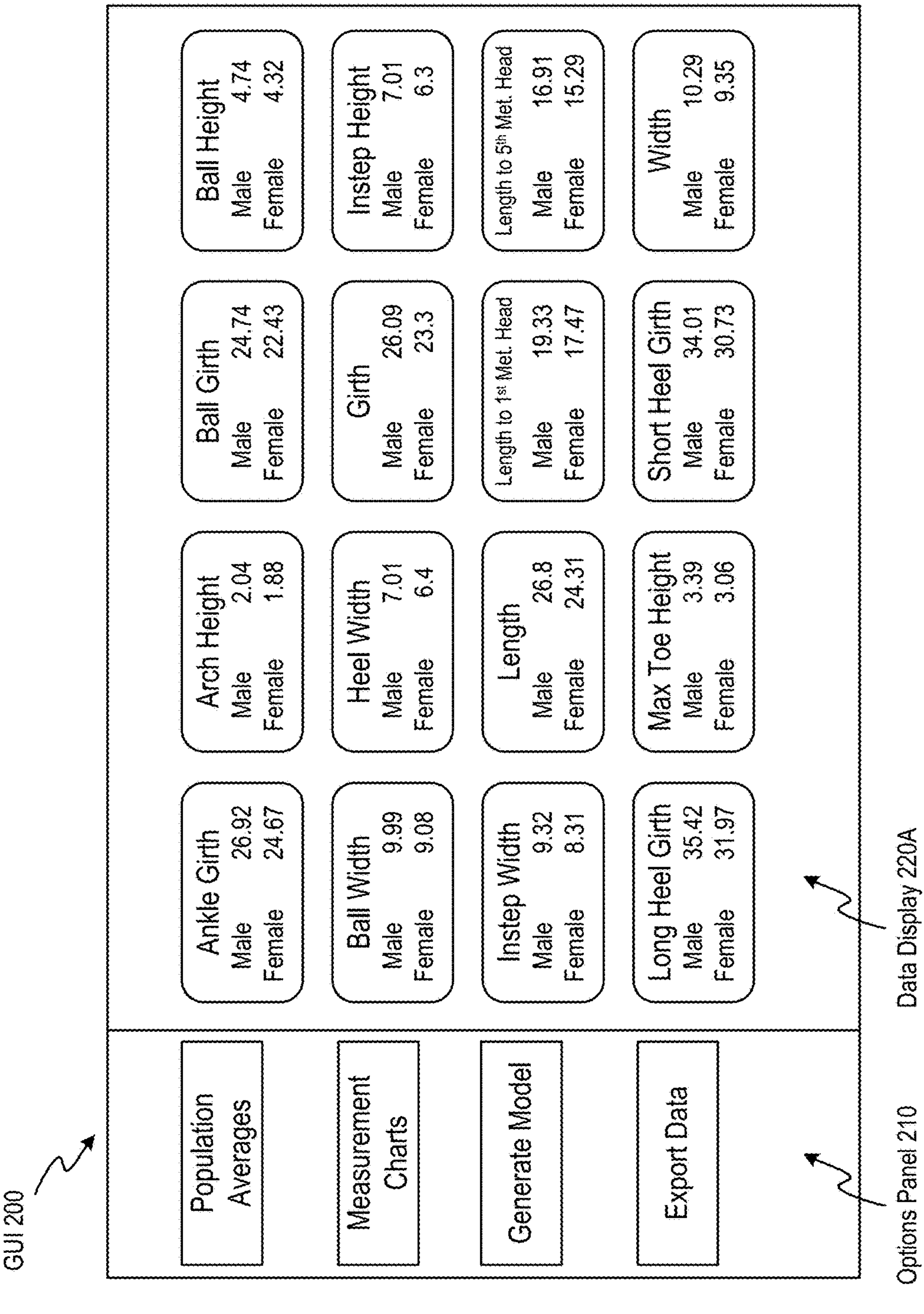
FIG. 2A illustrates an exemplary data display for providing a summary of statistical data in accordance with at least one embodiment.

In at least one embodiment, FIG. 2A illustrates an exemplary default landing page providing a summary of statistical data related to user/patient scans, shoe size distributions, and other relevant information. The data display 220A may also be presented for display in response to a user selection of the "Population Averages" option in the options panel 210.

The data shown in data display 220A may include one or more of numerical values corresponding to foot measurement data, histograms, geographic information, gender, or other information relevant to foot measurement data. In at least one embodiment, the foot measurement data may be retrieved, for example, by the data processing server 120 using the data management component 122 from the measurement data 132 of the data store 130, processed by the data processing server 120, and transmitted to the client device 110 for presentation by the user interface 112.

As shown in FIG. 2A, the data display 220A includes an arrangement of windows each corresponding to a particular foot measurement. In at least one embodiment, each window includes international statistical averages according to gender. In at least one embodiment, different data or arrangements of data may be displayed, such as statistical averages by region, percentile, or one or more other parameters. In at least one embodiment, the user may be presented with options for configuring the type of information to display in the data display 220A, for example, as the default landing page for the GUI 200.

Figure 2B:
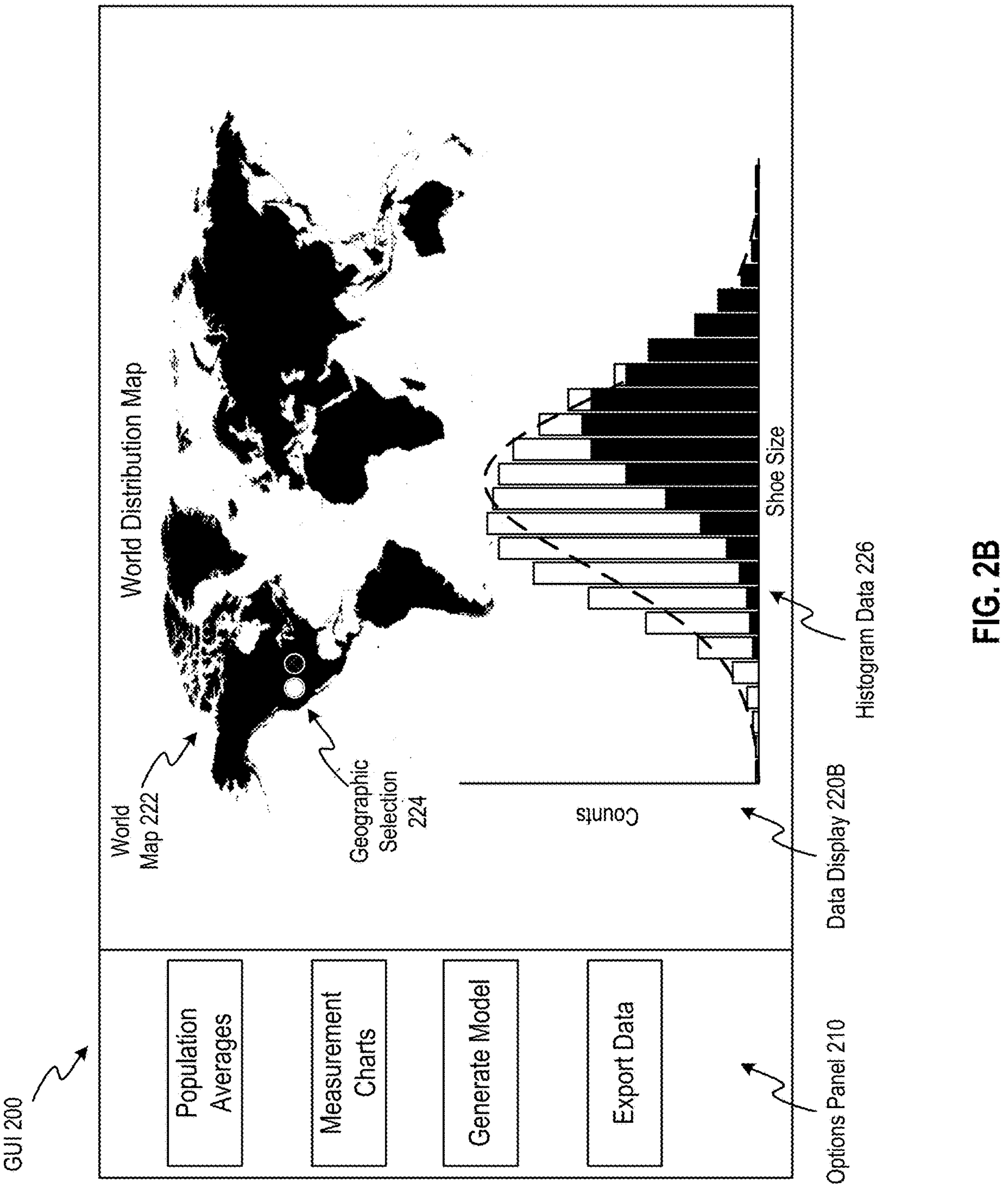
FIG. 2B illustrates an exemplary data display for displaying measurement chart data in accordance with at least one embodiment.

FIG. 2B illustrates an exemplary data display 220B for displaying measurement chart data in accordance with at least one embodiment. For example, the data display 220B may be displayed, for example, in response to a user selection of the "Measurement Charts" option from the options panel 210.

In at least one embodiment, the data display 220B includes a selectable world map 220 and one or more displays of histogram data 226. For example, in response to a geographic selection 224, indicated by the circular gender markers, the histogram data 226 may update to show regional statistical data for one or more sets of foot measurement data (e.g., shoe size) according to gender. In at least one embodiment, the user may select foot measurement data or related metrics selected from, but not limited to, length, width, girth, arch height, dorsal height, ankle girth, ball girth, ball height, ball width, heel width, instep width, length to first metatarsal head, length to fifth metatarsal head, long heel girth, short heal girth, and max toe height. In at least one embodiment, the user may make one or more geographic selection(s) 224 in the world map 222, which may compute averages. In at least one embodiment, the user may request an overlay on the histogram data 226, including, but not limited to, a Gaussian distribution curve (as shown), error bars, or other suitable metrics or indicators. In at least one embodiment, the data display 220B provides the user with control over the organization and visualization of the histogram data 226, such as options for changing bin size. In at least one embodiment, interaction with (e.g., by selecting, hovering over, etc.) one of the bins of the histogram data 226 may result in the display of information related to that bin, including the number of counts for that particular measurement within the processed dataset.

In at least one embodiment, selection of the "Export Data" option from the options panel 210 may provide the user with options for exporting selected sets or subsets of relevant foot measurement data, which may be downloadable in a spreadsheet format, such as a CSV file, an Excel spreadsheet, etc.

Figure 2C:
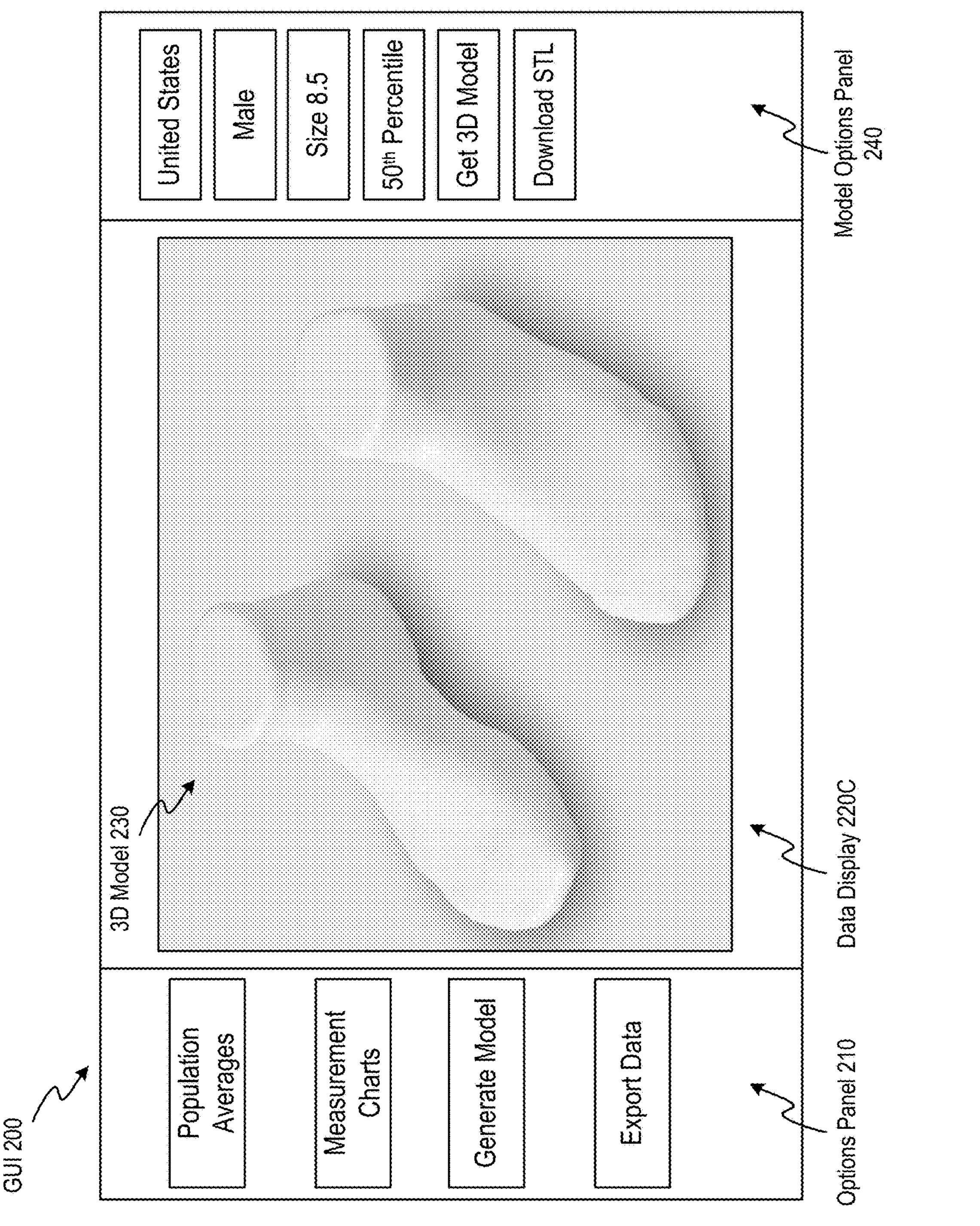
FIG. 2C illustrates an exemplary data display for generating and displaying a three-dimensional (3D) model of one or more feet or one or more foot lasts in accordance with at least one embodiment.

FIG. 2C illustrates an exemplary data display 220C for generating and displaying a 3D model 230 of one or more feet or one or more foot lasts in accordance with at least one embodiment. For example, the data display 220C may be displayed, for example, in response to a user selection of the "Generate Model" option from the options panel 210. In at least one embodiment, the user may select one or more options/parameters (e.g., geographic region(s), gender(s), shoe size(s), percentile(s), etc.) from the model options panel 240, which may result in re-generation of the 3D model 230 upon each selection. In at least one embodiment, selection of the "Get 3D Model" option from the model options panel 240 causes the 3D model 230 to be regenerated/refreshed. In at least one embodiment, selection of the "Download STL" option from the model options panel 240 can allow the user to download a file descriptive of the 3D model 230 (such as an STL file, or other suitable format).

Figure 2D:
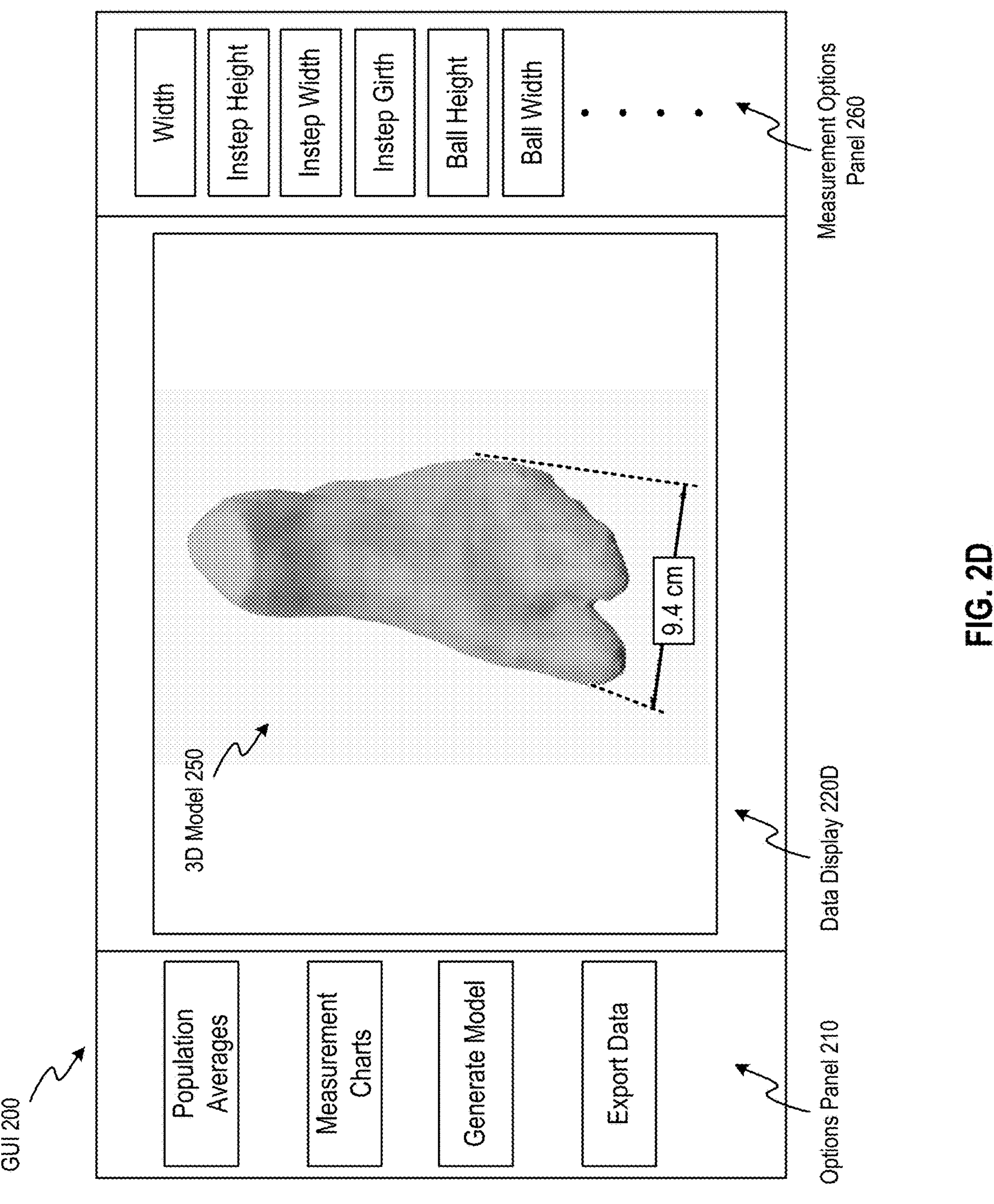
FIG. 2D illustrates an exemplary data display for characterizing dimensions of a 3D model of one or more feet or one or more foot lasts in accordance with at least one embodiment.

FIG. 2D illustrates an exemplary data display 220D for characterizing dimensions of a 3D model 250 in accordance with at least one embodiment. For example, the data display 220D may be displayed, for example, in response to a user selection of the "Generate Model" option from the options panel 210, or in response to user interaction with any 3D model displayed in the GUI 200. In at least one embodiment, selection of any of the options from the measurement options panel 260 may result in a visual display of those measurements within the data display 220D. For example, selection of the "Width" option from the measurement options panel 260 may result in the display of a measured width for the 3D model 250.

Figure 2E:
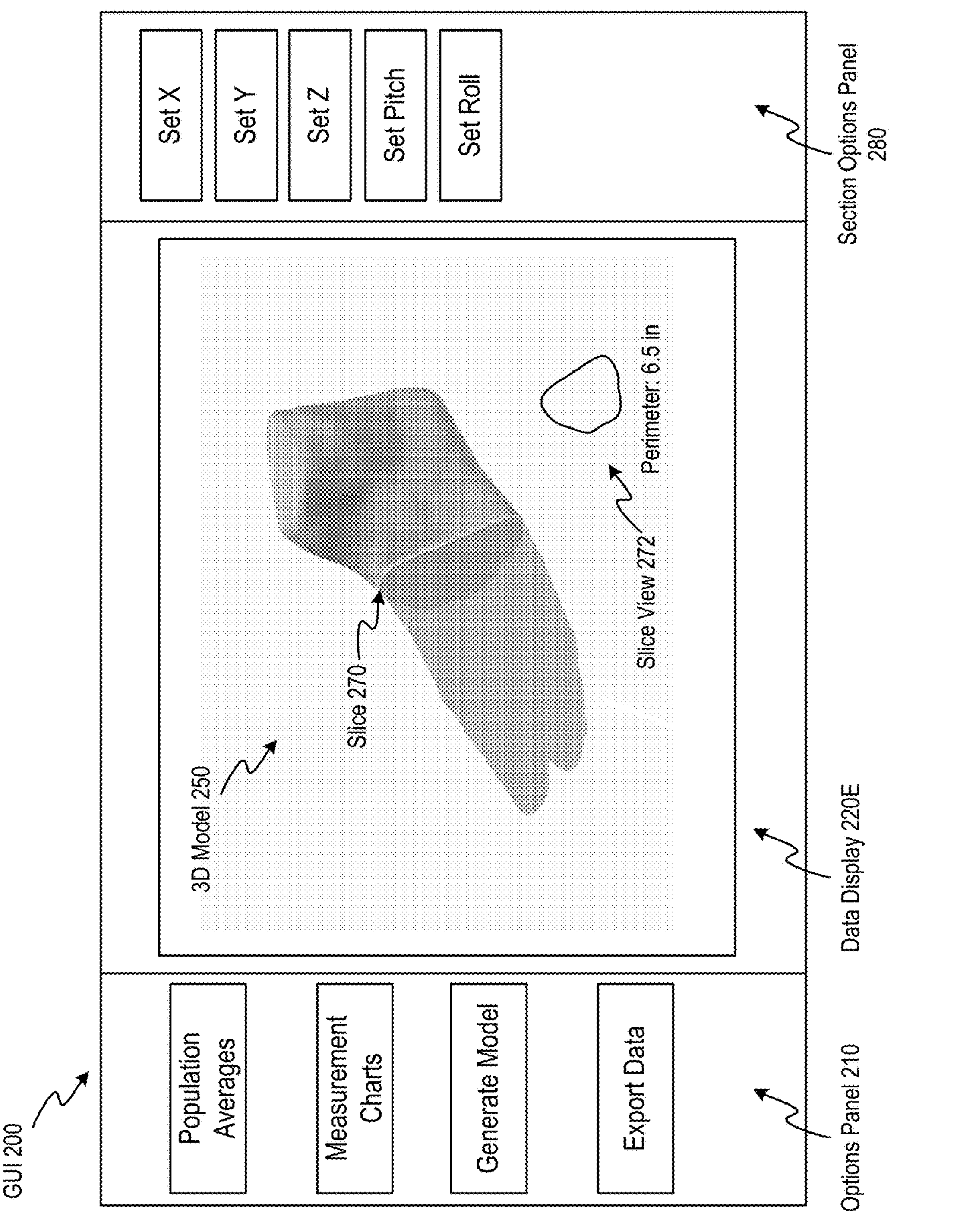
FIG. 2E illustrates an exemplary data display for characterizing a cross-section of a 3D model in accordance with at least one embodiment.

FIG. 2E illustrates an exemplary data display 220E for characterizing a cross-section of the 3D model 250 in accordance with at least one embodiment. For example, the data display 220E may be displayed, for example, in response to a user selection of the "Generate Model" option from the options panel 210, or in response to user interaction with any 3D model displayed in the GUI 200. In at least one embodiment, the user may select one or more options from the section options panel 280 to adjust any one of five degrees of freedom, including x, y, and z positions, pitch, and roll. In at least one embodiment, manipulation of any of these options may result in a corresponding change to the slice 270 with respect to the 3D model 250. For example, adjusting the y position may result in the slice 270 moving forward or backward along the length of the 3D model 250. In at least one embodiment, a slice view 272 may also be displayed concurrently to illustrate a flat view of the boundary at the intersection of the 3D model 250 and the slice 270. In at least one embodiment, a path length or perimeter may be displayed alongside the slice view 272.

Figure 3:
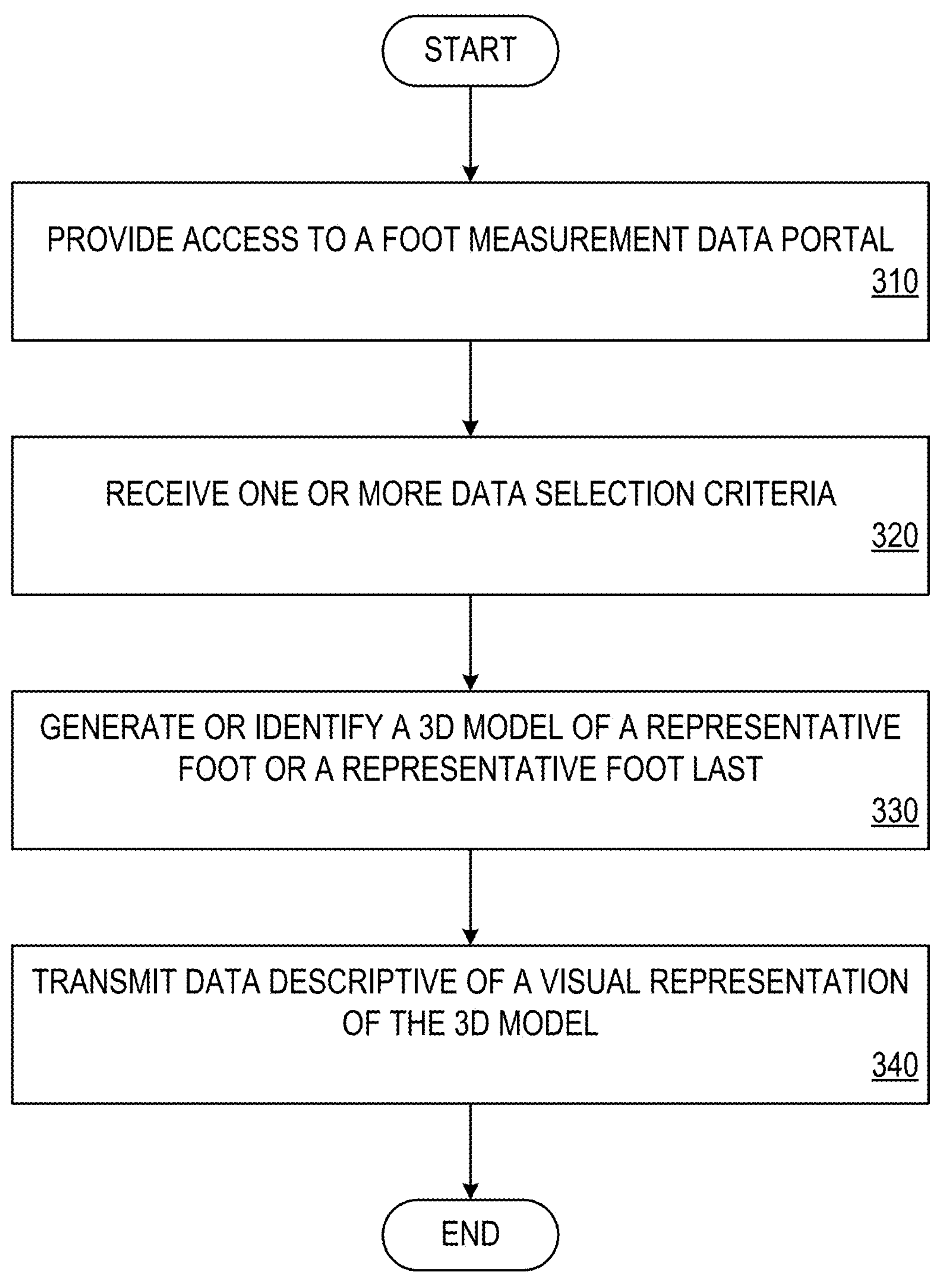
FIG. 3 is a block diagram illustrating a method for providing a user portal to facilitate modeling of foot-related data in accordance with at least one embodiment.

FIG. 3 is a block diagram illustrating a method 300 for providing a user portal to facilitate modeling of foot-related data in accordance with at least one embodiment. In at least one embodiment, the method 300 is implemented by the data processing server 120. In other embodiments, some or all of the elements of the method 300 are performed by the client device 110 and/or another device.

The method 300 begins at block 310, where a server (e.g., the data processing server 120) provides to a client device (e.g., the client device 110) access to a foot measurement data portal, which is presented to a user of the client device as a GUI (e.g., the GUI 200). For example, the GUI may provide any of the functionality described with respect to FIGS. 2A-2E.

At block 320, the server receives one or more data selection criteria corresponding to input of the user via the GUI. In at least one embodiment, the one or more data selection criteria comprise a selection (e.g., using model options panel 240 within the GUI 200) of one or more foot measurements selected from the group consisting of: length, width, girth, arch height, dorsal height, ankle girth, ball girth, ball height, ball width, heel width, instep width, length to first metatarsal head, length to fifth metatarsal head, long heel girth, short heal girth, and max toe height. In at least one embodiment, the selection criteria may also include a selection of various data filtering parameters, such as a gender, one or more geographic locations, one or more shoe sizes or a range thereof, and one or more percentiles. In at least one embodiment, the one or more data selection criteria comprise a user selection of a subset of foot measurement data from or corresponding to at least one data distribution (e.g., data corresponding to the histogram data 226). In at least one embodiment, the data selection criteria comprises a selection of output options, including whether the output corresponds to a 3D model of a representative foot or a 3D model of a representative foot last.

At block 330, the server generates or identifies a 3D model of a representative foot or a representative foot last based on the data selection criteria.

At block 340, the server transmits data descriptive of a visual representation of the 3D model to the client device for display via the GUI (e.g., the 3D model 230 as presented by the data display 220C).

In at least one embodiment, if the data selection criteria comprise a selection of a 3D model of a representative foot last as output, the server may transmit data descriptive of the 3D model to a fabrication device (e.g., the fabrication device 140) to fabricate the representative foot last, for example, responsive to a user request.

In at least one embodiment, the server identifies a 3D model of the representative foot or the representative foot last (e.g., by retrieving a prior generated model from model data 134). In at least one embodiment, the server identifies the 3D model by selecting the model for which the data selection criteria are a best fit using a suitable fitting algorithm. For example, if the selection specify the United States as the geographic location, male as the gender, a shoe size, ball width as the measurement, and a 75th percentile, the model generation component may identify a model corresponding to male feet in the United States for the particular shoe size and having a ball width within the 75th percentile. In at least one embodiment, the server may utilize a trained machine learning model to identify the prior generated model that best fits the one or more data selection criteria.

In at least one embodiment, the server identifies a 3D model of the representative foot or the representative foot last. For example, the 3D model may represent a best fit, or may be a generic model that is not correlated with the data selection criteria. In at least one embodiment, the server (e.g., via the model generation component 124) applies one or more transformation/deformation operations to the 3D model comprising, but not limited to, scaling, skewing, deforming, bending, or smoothing, in order to cause the dimensions of the 3D model to be a best fit or near best fit to the data selection criteria. For example, if the selection criteria require a specific heel width or range of heel widths, one or more transformations may be applied locally to a heel region represented by the 3D model in order to conform the corresponding measurements to the data selection criteria.

In at least one embodiment, the server transmits, to the user device, data descriptive of the 3D model for display to the user via the GUI, and receives a user selection of a planar slice through the 3D model (e.g., slice 270 as depicted in data display 220E). In at least one embodiment, the server computes a length of a path corresponding to an intersection of a planar slice through the 3D model, and computes a length of the path corresponding to the intersection (e.g., as depicted by the slice view 272).

For simplicity of explanation, methods and processes herein are depicted and described as a series of acts. However, acts in accordance with this disclosure can occur in various orders and/or concurrently and with other acts not presented and described herein. Furthermore, not all illustrated acts may be performed to implement the methods and processes in accordance with the disclosed subject matter. In addition, those skilled in the art will understand and appreciate that the methods and processes could alternatively be represented as a series of interrelated states via a state diagram or events.

Exemplary Computer System Embodiments

Figure 4:
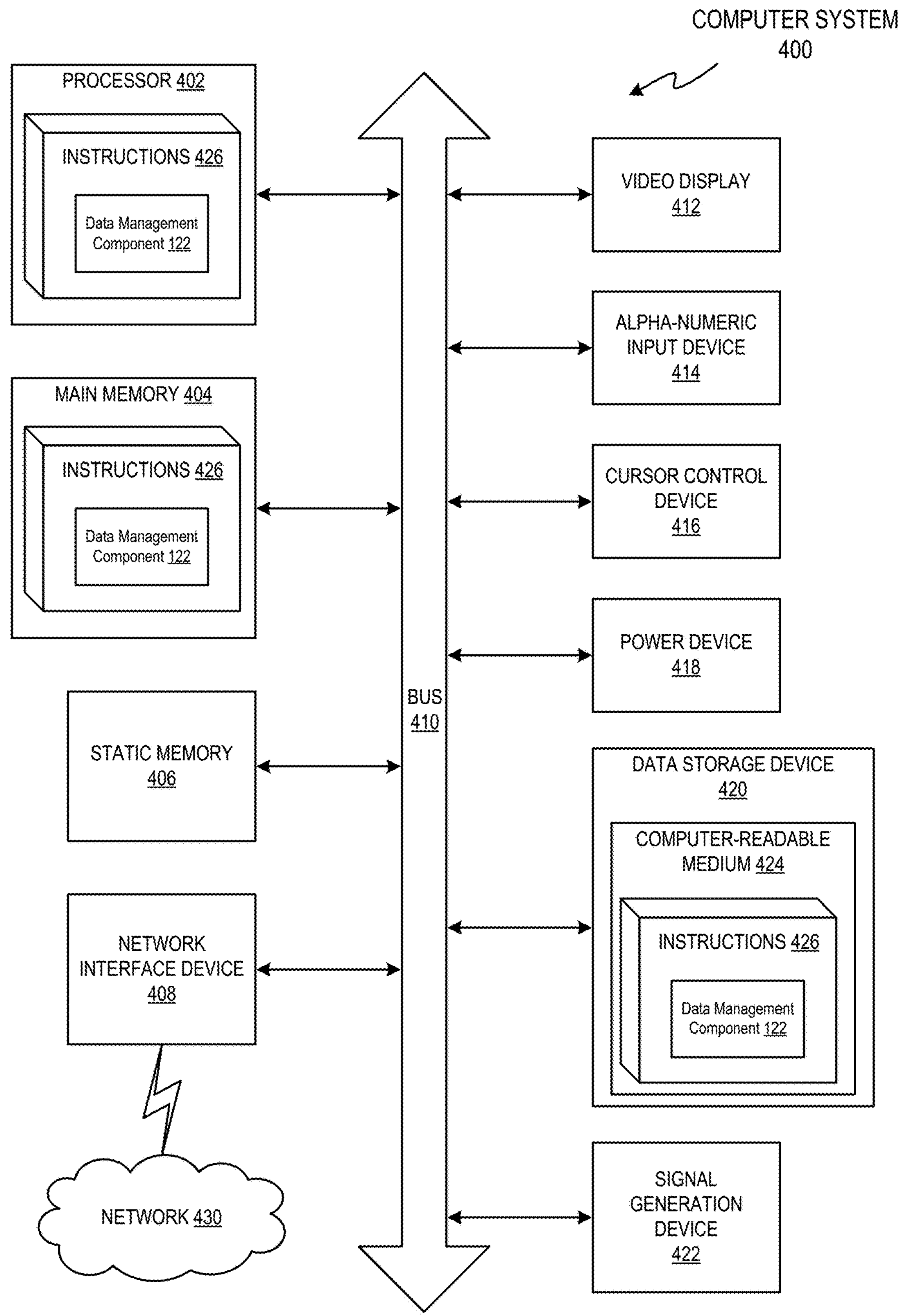
FIG. 4 is a block diagram illustrating an exemplary computer system for use in accordance with the various embodiments described herein.

FIG. 4 illustrates a diagrammatic representation of a machine in the exemplary form of a computer system 400 within which a set of instructions (e.g., for causing the machine to perform any one or more of the methodologies discussed herein) may be executed. In alternative embodiments, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term “machine” shall also be taken to include any collection of machines that individually or jointly execute a set (or multiple sets) of instructions to perform any one or more of the methodologies discussed herein. Some or all of the components of the computer system 400 may be utilized by or illustrative of at least some of the devices of the system architecture 100, such as the client device 110, the data processing server 120, the data store 130, or the fabrication device 140.

The exemplary computer system 400 includes a processing device (processor) 402, a main memory 404 (e.g., read-only memory (ROM), flash memory, dynamic random access memory (DRAM) such as synchronous DRAM (SDRAM) or Rambus DRAM (RDRAM), etc.), a static memory 406 (e.g., flash memory, static random access memory (SRAM), etc.), and a data storage device 420, which communicate with each other via a bus 410.

Processor 402 represents one or more general-purpose processing devices such as a microprocessor, central processing unit, or the like. More particularly, the processor 402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 402 may also be one or more special-purpose processing devices such as an ASIC, a field programmable gate array (FPGA), a digital signal processor (DSP), network processor, or the like. The processor 402 is configured to execute instructions 426 for performing the operations and steps discussed herein, such as operations associated with the data management component 122 or the model generation component 126.

The computer system 400 may further include a network interface device 408. The computer system 400 also may include a video display unit 412 (e.g., a liquid crystal display (LCD), a cathode ray tube (CRT), or a touch screen), an alphanumeric input device 414 (e.g., a keyboard), a cursor control device 416 (e.g., a mouse), and/or a signal generation device 422 (e.g., a speaker).

Power device 418 may monitor a power level of a battery used to power the computer system 400 or one or more of its components. The power device 418 may provide one or more interfaces to provide an indication of a power level, a time window remaining prior to shutdown of computer system 400 or one or more of its components, a power consumption rate, an indicator of whether computer system is utilizing an external power source or battery power, and other power related information. In at least one embodiment, indications related to the power device 418 may be accessible remotely (e.g., accessible to a remote back-up management module via a network connection). In at least one embodiment, a battery utilized by the power device 418 may be an uninterruptable power supply (UPS) local to or remote from computer system 400. In such embodiments, the power device 418 may provide information about a power level of the UPS.

The data storage device 420 may include a computer-readable storage medium 424 on which is stored one or more sets of instructions 426 (e.g., software) embodying any one or more of the methodologies or functions described herein. The instructions 426 may also reside, completely or at least partially, within the main memory 404 and/or within the processor 402 during execution thereof by the computer system 400, the main memory 404 and the processor 402 also constituting computer-readable storage media. The instructions 426 may further be transmitted or received over a network 430 (e.g., the network 105) via the network interface device 408.

In one embodiment, the instructions 426 include instructions for implementing the functionality of the data processing server 120, as described throughout this disclosure. While the computer-readable storage medium 424 is shown in an exemplary embodiment to be a single medium, the terms “computer-readable storage medium” or “machine-readable storage medium” should be taken to include a single medium or multiple media (e.g., a centralized or distributed database, and/or associated caches and servers) that store the one or more sets of instructions. The terms “computer-readable storage medium” or “machine-readable storage medium” shall also be taken to include any transitory or non-transitory medium that is capable of storing, encoding or carrying a set of instructions for execution by the machine and that cause the machine to perform any one or more of the methodologies of the present disclosure. The term “computer-readable storage medium” shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the preceding discussion, it is appreciated that throughout the description, discussions utilizing terms such as "configuring," "receiving," "converting," "causing," "streaming," "applying," "masking," "displaying," "retrieving," "transmitting," "providing," "computing," "generating," "adding," "subtracting," "multiplying," "dividing," "selecting," "parsing," "optimizing," "calibrating," "detecting," "storing," "performing," "analyzing," "determining," "enabling," "identifying," "modifying," "transforming," "aggregating," "extracting," "running," "scheduling," "processing," "capturing," "evolving," "fitting," "segmenting," "deriving," "training," "presenting," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including floppy disks, optical disks, compact disk read-only memories (CD-ROMs), and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "certain embodiments," "one embodiment," "at least one embodiment," or the like means that a particular feature, structure, or characteristic described in connection with the embodiment is included in at least one embodiment. Thus, the appearances of the phrase "certain embodiments," "one embodiment," "at least one embodiment," or the like in various places throughout this specification are not necessarily all referring to the same embodiment.

The present disclosure is not to be limited in scope by the specific embodiments described herein. Indeed, other various embodiments of and modifications to the present disclosure, in addition to those described herein, will be apparent to those of ordinary skill in the art from the description and accompanying drawings. Thus, such other embodiments and modifications are intended to fall within the scope of the present disclosure. Further, while the present disclosure has been described in the context of a particular embodiment in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein, along with the full scope of equivalents to which such claims are entitled.

What is claimed is:

1. A method comprising:

providing, to a client device by a server, access to a foot measurement data portal presented to a user of the client device as a graphical user interface (GUI);

receiving, by the server, one or more data selection criteria corresponding to input of the user via the GUI;

generating or identifying, by the server, a three-dimensional (3D) model of a representative foot or a representative foot last based on the data selection criteria, wherein the 3D model of the representative foot or the representative foot last is generated or identified by fitting to statistical data identified based on the data selection criteria; and transmitting, to the client device, data descriptive of a visual representation of the 3D model for display via the GUI.

2. The method of claim 1, wherein the 3D model corresponds to the representative foot last, and wherein the method further comprises:

transmitting data descriptive of the 3D model to a fabrication device to fabricate the representative foot last.

3. The method of claim 1, wherein the one or more data selection criteria comprise a user selection of a subset of foot measurement data from at least one data distribution.

4. The method of claim 1, wherein the one or more data selection criteria comprise a selection of one or more foot measurements selected from the group consisting of: length, width, girth, arch height, dorsal height, ankle girth, ball girth, ball height, ball width, heel width, instep width, length to first metatarsal head, length to fifth metatarsal head, long heel girth, short heal girth, and max toe height.

5. The method of claim 1, wherein identifying the 3D model of the representative foot or the representative foot last comprises identifying, by a trained machine learning model, a prior generated 3D model that best fits the one or more data selection criteria.

6. The method of claim 1, wherein generating the 3D model of the representative foot or the representative foot last comprises generating the 3D model by applying one or more transformations to a 3D model of a foot identified or generated, by a trained machine learning model, as a best fit to the one or more data selection criteria.

7. The method of claim 1, further comprising:

transmitting, to the user device, data descriptive of the 3D model for display to the user via the GUI;

receiving, by the server, a user selection of a planar slice through the 3D model; and computing a length of a path corresponding to an intersection of the planar slice and the 3D model.

8. A system comprising:

at least one memory unit; and a processing device operatively coupled to the at least one memory unit, wherein the processing device is configured to:

provide, to a client device, access to a foot measurement data portal presented to a user of the client device as a graphical user interface (GUI);

receive one or more data selection criteria corresponding to input of the user via the GUI;

generate or identify a three-dimensional (3D) model of a representative foot or a representative foot last based on the data selection criteria, wherein the 3D model of the representative foot or the representative foot last is generated or identified by fitting to statistical data identified based on the data selection criteria; and transmit, to the client device, data descriptive of a visual representation of the 3D model for display via the GUI.

9. The system of claim 8, wherein the 3D model corresponds to the representative foot last, and wherein the processing device is further configured to:

transmit data descriptive of the 3D model to a fabrication device to fabricate the representative foot last.

10. The system of claim 8, wherein the one or more data selection criteria comprise a user selection of a subset of foot measurement data from at least one data distribution.

11. The system of claim 8, wherein the one or more data selection criteria comprise a selection of one or more foot measurements selected from the group consisting of: length, width, girth, arch height, dorsal height, ankle girth, ball girth, ball height, ball width, heel width, instep width, length to first metatarsal head, length to fifth metatarsal head, long heel girth, short heal girth, and max toe height.

12. The system of claim 8, wherein identifying the 3D model of the representative foot or the representative foot last comprises identifying, by a trained machine learning model, a prior generated 3D model that best fits the one or more data selection criteria.

13. The system of claim 8, wherein generating the 3D model of the representative foot or the representative foot last comprises generating the 3D model by applying one or more transformations to a 3D model of a foot identified or generated, by a trained machine learning model, as a best fit to the one or more data selection criteria.

14. The system of claim 8, wherein the processing device is further configured to:

transmit, to the user device, data descriptive of the 3D model for display to the user via the GUI;

receive a user selection of a planar slice through the 3D model; and compute a length of a path corresponding to an intersection of the planar slice and the 3D model.

15. A non-transitory computer-readable medium having instructions encoded thereon that, when executed by a processing device, cause the processing device to:

provide, to a client device, access to a foot measurement data portal presented to a user of the client device as a graphical user interface (GUI);

receive one or more data selection criteria corresponding to input of the user via the GUI;

generate or identify a three-dimensional (3D) model of a representative foot or a representative foot last based on the data selection criteria, wherein the 3D model of the representative foot or the representative foot last is generated or identified by fitting to statistical data identified based on the data selection criteria; and transmit, to the client device, data descriptive of a visual representation of the 3D model for display via the GUI.

16. The non-transitory computer-readable medium of claim 15, wherein the 3D model corresponds to the representative foot last, and wherein the instructions further cause the processing device to:

transmit data descriptive of the 3D model to a fabrication device to fabricate the representative foot last.

17. The non-transitory computer-readable medium of claim 15, wherein the one or more data selection criteria comprise a user selection of a subset of foot measurement data from at least one data distribution, and wherein the one or more data selection criteria comprise a selection of one or more foot measurements selected from the group consisting of: length, width, girth, arch height, dorsal height, ankle girth, ball girth, ball height, ball width, heel width, instep width, length to first metatarsal head, length to fifth metatarsal head, long heel girth, short heal girth, and max toe height.

18. The non-transitory computer-readable medium of claim 15, wherein identifying the 3D model of the representative foot or the representative foot last comprises identifying, by a trained machine learning model, a prior generated 3D model that best fits the one or more data selection criteria.

19. The non-transitory computer-readable medium of claim 15, wherein generating the 3D model of the representative foot or the representative foot last comprises generating the 3D model by applying one or more transformations to a 3D model of a foot identified or generated, by a trained machine learning model, as a best fit to the one or more data selection criteria.

20. A method comprising:

providing, to a client device by a server, access to a foot measurement data portal presented to a user of the client device as a graphical user interface (GUI);

presenting, for display in the GUI, a three-dimensional (3D) model of a foot or a foot last, wherein the 3D model of the foot or the foot last is generated or identified by fitting to statistical data;

receiving, by the server, a user selection of a planar slice through the 3D model, the user selection comprising a position and an orientation of the planar slice with respect to the 3D model;

computing a length of a path corresponding to an intersection of the planar slice and the 3D model; and presenting, for display in the GUI, the computed length.

* * * * *